(12) United States Patent
Ernst et al.

(10) Patent No.: US 8,920,344 B2
(45) Date of Patent: Dec. 30, 2014

(54) MOBILE BALANCING PROSTHESIS

(76) Inventors: Arneborg Ernst, Berlin (DE); Dietmar Basta, Brieselang (DE)

( * ) Notice: Subject to any disclaimer, the term of this patent is extended or adjusted under 35 U.S.C. 154(b) by 1318 days.

(21) Appl. No.: 12/296,619

(22) PCT Filed: Apr. 10, 2007

(86) PCT No.: PCT/DE2007/000646
§ 371 (c)(1),
(2), (4) Date: Feb. 18, 2009

(87) PCT Pub. No.: WO2007/115565
PCT Pub. Date: Oct. 18, 2007

(65) Prior Publication Data
US 2009/0192416 A1 Jul. 30, 2009

Related U.S. Application Data

(60) Provisional application No. 60/867,002, filed on Nov. 22, 2006.

(30) Foreign Application Priority Data

Apr. 10, 2006 (DE) .......................... 10 2006 017 221
May 27, 2006 (EP) ..................................... 06010903

(51) Int. Cl.
*A61B 5/103* (2006.01)
*A61B 5/00* (2006.01)
*A61B 5/11* (2006.01)

(52) U.S. Cl.
CPC ............. *A61B 5/1116* (2013.01); *A61B 5/6831* (2013.01); *A61B 5/1124* (2013.01); *A61B 5/6823* (2013.01); *A61B 2562/046* (2013.01); *A61B 5/4023* (2013.01); *A61B 2505/09* (2013.01); *A61B 2503/10* (2013.01)
USPC .......................................................... 600/595

(58) Field of Classification Search
CPC ............... A61B 5/0059; A61B 5/0066; A61B 5/14535; G01N 21/359; G01N 21/4795; G01N 2021/1782
USPC .................................................. 600/587, 592
See application file for complete search history.

(56) References Cited

U.S. PATENT DOCUMENTS

| 3,612,060 A | 10/1971 | Colyer |
| 4,092,633 A | 5/1978 | Fletcher et al. |
| 5,197,489 A * | 3/1993 | Conlan .......................... 600/595 |

(Continued)

FOREIGN PATENT DOCUMENTS

| EP | 1 366 712 A1 | 12/2003 |
| EP | 1 400 438 A2 | 3/2004 |

(Continued)

OTHER PUBLICATIONS

Analog Devices ADXRS150 Data sheet, 2004.*

*Primary Examiner* — Sean Dougherty
*Assistant Examiner* — Michael C Stout
(74) *Attorney, Agent, or Firm* — Joyce von Natzmer; Agris & von Natzmer LLP (57) ABSTRACT

The invention is directed to a mobile balancing device and the use of said balancing device for the balance training of a body; the invention is further directed to a method for mobile balance training, e.g. for athletes or patients.

19 Claims, 5 Drawing Sheets a           b

(56) References Cited

U.S. PATENT DOCUMENTS

| | | | |
|---|---|---|---|
| 5,281,957 A | 1/1994 | Schoolman | |
| 5,361,778 A | 11/1994 | Seitz | |
| 5,469,861 A | 11/1995 | Piscopo et al. | |
| 5,919,149 A * | 7/1999 | Allum | 600/595 |
| 6,148,700 A * | 11/2000 | Upholz | 81/486 |
| 6,488,794 B1 * | 12/2002 | Bright et al. | 156/86 |
| 6,546,291 B2 * | 4/2003 | Merfeld et al. | 607/62 |
| 6,997,882 B1 * | 2/2006 | Parker et al. | 600/534 |
| 7,016,473 B1 * | 3/2006 | Linev et al. | 378/146 |
| 7,713,217 B2 * | 5/2010 | Ikeuchi et al. | 600/595 |
| 2002/0010497 A1 * | 1/2002 | Merfeld et al. | 607/62 |
| 2003/0208409 A1 * | 11/2003 | Mault | 705/26 |
| 2003/0234623 A1 * | 12/2003 | Douglas | 318/254 |
| 2004/0116837 A1 * | 6/2004 | Yamaguchi et al. | 600/595 |
| 2005/0052852 A1 * | 3/2005 | Ono | 361/749 |
| 2006/0195050 A1 * | 8/2006 | Alwan et al. | 600/595 |
| 2006/0195051 A1 * | 8/2006 | Schnapp et al. | 600/595 |
| 2007/0032748 A1 * | 2/2007 | McNeil et al. | 600/595 |
| 2007/0038268 A1 * | 2/2007 | Weinberg et al. | 607/62 |
| 2007/0073196 A1 * | 3/2007 | Tanaka et al. | 600/595 |
| 2009/0192414 A1 * | 7/2009 | Yasuhara | 600/587 |

FOREIGN PATENT DOCUMENTS

| | | |
|---|---|---|
| EP | 1400138 A0 | 3/2004 |
| EP | 1 593 931 A1 | 11/2005 |
| GB | 1 385 954 | 3/1975 |
| WO | 8804909 A2 | 7/1988 |
| WO | 98/46127 A1 | 10/1998 |
| WO | 00/35345 A1 | 6/2000 |
| WO | 03001830 A1 | 1/2003 |
| WO | 2004/103176 A1 | 12/2004 |
| WO | 2005/002436 A1 | 1/2005 |

\* cited by examiner

MOBILE BALANCING PROSTHESIS

This application is the U.S. National Stage Entry of International Application PCT/DE2007/000646, filed Apr. 10, 2007, designating the U.S., which claims the benefit of U.S. Provisional Application 60/867,002, filed Nov. 22, 2006 and also claims priority to European Application No. 06010903.0, filed Mar. 27, 2006 and German Patent Application 102006017221.3, filed Apr. 10, 2006, all of which are incorporated herein by reference in their entireties.

The invention is directed to a mobile balancing device and to the use of said balancing device for the balance training of a body; the invention is further directed to a method for mobile balance training, e.g. for athletes or patients.

All organisms, especially vertebrates and, of these, particularly those that walk upright, have a specialized sense of balance. The sense of balance serves to determine posture and spatial orientation. In man, for example, it is centered in the equilibrium organ, in the inner ear and cerebellum, although it is closely linked to the eyes and other sense organs and to the reflexes. The sense of balance includes the sense of up and down (the plumb line direction), angles and tilts (postural orientation) and rhythm, as well as linear and rotational acceleration, especially of the head, in all directions. The sense of balance in man is completed by vision (for spatial position), the skeletal musculature (for extension and acceleration of the body), the buttocks (for acceleration primarily in the vertical direction), the hearing (for estimating speed on the basis of air sounds) and the cutaneous sense organs (for the movement of the body itself and for air movement during linear and rotational acceleration). The sense of balance can be disrupted by metabolic changes, disease and accidents, but also by natural processes such as ageing.

The prior art includes descriptions of a number of ways of treating an impaired sense of balance or training the patient so that he is only conditionally limited by balance impairment. If, for example, eye movement and postural reaction lie outside the limit values for good balance orientation, medication can be used to reduce the activity of peripheral equilibrioception in the brain. The affected person can then train his own brain to keep the body upright despite a diminished sense of balance. However, the drugs have numerous side effects, and this method consequently cannot always be used.

Numerous devices that can be used to train the sense of balance are described in the prior art. For instance, U.S. Pat. No. 4,092,633 describes a system for measuring movement status, comprising a detector that generates a pulse when a parameter of a monitored movement status exceeds a preset threshold. A resettable movement status meter counts each pulse, a specific time frame being set by a clock. The movement status meter generates a signal when the total number of pulses within the timeframe is greater than or equal to the preset number. In response to the incoming pulses and the movement status signal, a monitoring system generates control signals that control the system as a whole.

Other devices for analyzing characteristic movements associated with the sense of balance are described, for example, in U.S. Pat. No. 5,361,778, U.S. Pat. No. 5,469,861 and WO 8804909. DE 3416837 discloses a system for achieving an upright gait in which sensors and nerve stimulators are used, the system being controlled by a computer. U.S. Pat. No. 5,281,957 discloses a portable computer and a head-mounted, transparent display in the form of a pair of eyeglasses whose lenses are configured in the form of a liquid crystal display.

U.S. Pat. No. 5,919,149 discloses a mobile balancing prosthesis in which changes in body position are detected only two-dimensionally. WO 2004/103176 discloses a balancing means for purely diagnostic purposes, which cannot in its entirety be worn on the body. Moreover, this device is not able to receive signals representating changes in the angular velocity of a body. U.S. Pat. No. 3,612,060 describes a stimulator that is placed on the body of a patient who is under anesthesia. This device includes a portable low-power source for peripheral, but not central, nervous stimulation during general anesthesia. Disadvantageously, signals representing changes in angular velocity cannot be detected.

WO 98/46127 presents a rotatable and pivotable, and thus freely movable, platform for diagnosing and treating balance disorders. Feedback is possible during balance training on the rotating platform.

WO 2005/002436 describes a sensor system for recording force, particularly in connection with the lifting or carrying of loads. This system makes it possible to determine the angular-velocity acceleration of individual body segments with the aid of sensors worn on the body.

A technical device for correcting balance problems is discussed in EP 1 593 931. This device cannot be worn on the body, however, and is therefore only conditionally usable as a mobile device by a user.

EP 1 400 138, WO 00/35345 and GB 1 385 954 A disclose (i) means for detecting forces occurring in the joints of running bipeds, (ii) means for detecting lumbar lordosis and postural disorders, or alternatively (iii) implants for invasive electrostimulation. With these devices, it is impossible to detect either the variation of the angular velocity in a three-dimensional space, or the received signals representing an angular velocity determination are unrelated to the activity of possible actuators.

It is known that the functioning of the human equilibrium organ can be objectively quantified by monitoring various vestibular reflexes and by testing postural reactions in specific movement or test situations. The aim is to determine whether the values stay within the normal ranges that are to be expected with normal balance function. In the event of significant deviations from these normal ranges, drug therapy, surgical treatment or physical therapy is usually instituted, depending on the specific deficit diagnosed. These methods are not presently successful in every case, however. For instance, drug therapy (see above) cannot always be made specific, and thus, for the most part, merely alleviates dizziness. Due to the possibility of perioperative complications, surgery is the method of choice for very few disorders. The treatment usually includes a course of physical-therapy-oriented balance training. During such training units, the patient repeatedly subjects himself to defined borderline situations that destabilize the equilibrium organ, with the goal of improving balance control. In the course of these exercises (several months), patients develop more or less pronounced central nervous compensation for the altered balance information by relying on other sensory modalities (visual, somatosensory). In many patients, however, due to unexplained resistance to treatment or severity of disease, training of this kind does not suffice to bring about vestibular rehabilitation. Nevertheless, an improvement in balance control has been achieved in these patients by means of devices that convert data relating to changes in body position into a compensatory stimulus (e.g. visual, auditory) and then deliver these stimuli in amplified form to intact sensory inputs of the patient (e.g. the eye, the ear). Heretofore, this therapy has been place-bound and suitable only for training in certain predetermined tasks. No mobile device is available at present that is suitable for day-to-day use and can provide individual support to the equilibrium organ in every kind of day-to-day situation (e.g.

jogging, bicycling, etc.). Such a device should, above all, be capable of distinguishing voluntary movements of the wearer from movements caused by disturbances of equilibrium. Previous devices have been unable to do this. In addition, other sensory impressions should not be impaired or affected by the use of the device. These requirements, as well, have not been met by any device heretofore. Current devices have only a limited ability to function as a training aid or a prosthetic in the performance of a specific task. Moreover, the type of stimulation used in these devices (visual, gustatory or auditory) prevents them from being used on a day-to-day basis. In the devices available heretofore, inter alia the acceleration of body parts is measured, and if threshold values are exceeded, a signal is delivered. During running, bicycling or similar activities, linear accelerations occur that have nothing to do with maintaining balance. If this acceleration has an influence on the compensatory stimulus that is supplied, then the device is not suitable for use in day-to-day situations.

The pharmaceutical agents known in the prior art, like the devices and methods, do not make it possible to compensate in day-to-day situations for missing equilibrium data or spatial orientation data that enable the brain to determine the body's position in space and thus introduce any postural correction that may be necessary. The devices known from the prior art also are not such that they can be used as training devices in the rehabilitative treatment of balance disorders and/or as balance prostheses to prevent falls and/or to control posture.

The object of the invention was to provide a means that does not have the disadvantages of the prior art.

The object is achieved by means of a mobile balancing device, said balancing device being so configured that it preferably can be worn as a belt around the waist and comprises a gyrometer that three-dimensionally determines changes in a body position as changes in the angular velocity of forward, backward and/or sideward movements of the body, and the signals representing the angular velocity determination are proportional to the activity of the actuators, and the activation of the actuators is substantially suppressed when the values of the angular velocity are within limits assigned to said angular velocity values on the basis of the movement sequence.

The teaching according to the application presents a number of advantages over the prior art:
  a turning away from standard technical expedients
  a new statement of object (simultaneous solving of the problem of balance disorders and [use] as a balance prosthesis for fall prevention or posture control)
  the existence of a long-unmet, urgent need for the solution to the problem solved by the invention
  fruitless efforts heretofore by those skilled in the art
  the simplicity of the solution argues in favor of an inventive step, especially since it replaces complex teaching
  development within the art was heading in a different direction
  the effect of tightening development
  misconceptions of the skilled community regarding the solution to the problem in question (prejudice)
  technical progress, such as, for example: improvement, higher performance, price reduction, saving of time, material, work steps, costs or hard-to-obtain raw materials, increased reliability, elimination of defects, quality improvement, freedom from maintenance, greater effectiveness, higher yield, multiplication of technical options, provision of another means, opening up of a second path, opening up of a new field, first solution of a problem, back-up means, alternatives, way of achieving streamlining, automation or miniaturization
  error in reference citations
  young field of technology
  combination invention, i.e., a number of known elements are brought together and yield a surprising effect
  licensing
  praise from those skilled in the art and
  economic success.

Particularly the advantageous embodiments of the invention display at least one, or more, of the aforesaid advantages.

One major advantage of the inventive balancing device is that changes in body position can be determined at rest and in motion in space. The measurement data are first acquired two-dimensionally, and are then converted to a three-dimensional spatial presentation using the mathematical formula given below. The accompanying data presented in Table 1 substantiate the individual- and sequence-specific specificity of the inventive device and of the measurement data acquired with it. The inventive device is more specific than the devices known from the prior art. Its very good programmability and outstanding customizability are evidenced by the age- and sex-specific database for specific movement sequences that has been filed (Table 1). The device can thus be used even outside the medical and rehabilitation field. Owing to its comprehensive programmability, this is also possible in areas where a healthy sense of balance is to be improved further, such as the case of balance exercises in sports or the training of paratroopers by the military. A particular advantage is the processing of the signals into three-dimensional spatial information. A modulator or adjustment knob serves, in this connection, to activate different programs (e.g. 1 to 5), which then, depending on the design, activate the actuator over a range of "very mild" (e.g. in the case of a gymnast working to improve his or her balancing ability) to "very strong" (e.g. in the case of a patient after a stroke, where parts of the balance center are destroyed). Advantageously, the inventive device has a surprisingly wide range of system versatility, since it can be used in the below-normal range, e.g. for gymnasts, or in the above-normal range, for severely ill patients. Another advantage, one that has already been discussed, is free programmability through the selection of individual movement programs, supported by the normal values and the database according to Table 1.

The balancing prosthesis can advantageously be worn on the middle of the body and can preferably include a sensor that describes the spatial displacement vector ($a=(a_1, a_2, a_3)$). The displacement vector in the spatial planes is determined by movements of the body, preferably by means of gyrometers that are disposed orthogonally to each other. The maximum value of the spatial displacement vector determined by means of the invention is constant (normal value) for a specific movement sequence, and is equated with an electrical resistance. The strength of this electrical resistance is advantageously so high, in a particular embodiment of the invention, that the activity of connected stimulators (actuators) is equal to zero. Conversely, the stimulators (actuators) are activated as soon as the normal value of the spatial displacement vector is exceeded. The values assumed by all the spatial displacement vectors during a specific, complex movement sequence can preferably be corrected uniformly and centrally by increasing or decreasing the corresponding resistances with an adjustment knob.

The individual programs are freely adjustable in terms of the positions of the body in space. Advantageously, there is, therefore, no simple, linearly proportional relationship between the actuation of the gyrometers and the actuation of the actuators. Actuators in the sense of the invention are preferably balance-wheel motors such as Pager Motor 6CH- 1201-WL-00, Namiko Corp., Tokyo. The rotation speed of balance-wheel motor in this case is preferably dependent on the frequency of the delivered pulses. The duty factor of the delivered pulses is 50% in a preferred embodiment of the invention. If this is not possible, then the pulse width of the negative or positive portion of the pulse should be no less than 5 µs. In a particularly preferred embodiment of the invention, the balance-wheel motor has a resolution of 1.8°. In this context, the driver electronics can drive the motor using microstep technology. It can advantageously be adjusted so that 64 pulses advance the drive shaft 1.8°, the frequency of the pulse thus being calculated as follows:

$$f[1/s] = \frac{X[°/s]}{1.8°} \times 64$$

where X [°/s]=desired angular velocity;
1.8°=basic resolution of the step width of the motor
64=fine resolution of the basic resolution of the step width of the motor.

The motor is preferably to be activated at the nominal rotation speed for a period of about one second. In a particularly preferred embodiment of the invention, the frequency (f) should not exceed 25 kHz.

Surprisingly, the inventive device does not possess the disadvantages of the prior art. It constitutes a mobile device that is suitable for day-to-day use and can provide individual support for the balance system in all day-to-day situations. This device is capable of distinguishing voluntary movements of the wearer from movements caused by disturbances of equilibrium.

Thus, the teaching according to the invention makes available a mobile, programmable device that serves to compensate, in day-to-day situations, for missing equilibrium data and/or orientation data that enable the brain to determine the body's position and introduce a correction. The device's measurement and integration unit advantageously measures changes in the angular velocity (the Coriolis force) of the body or of a body part in two spatial planes (x; y) by means of gyrometers. It was completely surprising to find that gyrometers can be used to train a person's sense of balance if the measurement data are converted to a three-dimensional spatial presentation using the above formula (see example, also).

In a preferred variant of the invention, stimulators placed on the body are activated when the body part on which the device is being worn moves faster than is authorized by a movement-specific, personal program. In one advantageous embodiment, this program is a set of signal attenuators connected downstream of the four outputs of each gyrometer (back, front, left, right). It may also be advantageous, however, if signal amplifiers are connected downstream of the four gyrometer outputs.

The program is specific in each case to an action or a movement sequence of an individual wearer. The program suitable for monitoring posture is activated for the corresponding action or movement sequence by the wearer, for example manually or by voice command, or automatically by the device, for example by having it recognize movement sequences by analyzing brain or muscle activity. By means of this this preferred program choice, the strength of the attenuation is adapted to specific circumstances or, alternatively, gyrometer output signals that generate a pattern of stimulator actuation thresholds are activated or increased, with the result that activities and actions within the scope of voluntary motor function remain stimulation-free.

In a particularly preferred embodiment of the invention, the actuators are balance-wheel motors. It is preferred that the rotation speed of the balance-wheel motor depend on the frequency of an outgoing pulse. It is particularly advantageous if the movements of the body are determined as displacement vectors (a=($a_1$, $a_2$, $a_3$)) by means of gyrometers that are disposed orthogonally to each other.

In another preferred embodiment of the invention, the balancing device is characterized by the fact that changes in body position for a third reference axis are calculated as follows:

$$\alpha' = \arccos \frac{(b'^2 + c'^2 - a'^2)}{2b'c'}$$

where:

$$a' = \frac{b}{\cos(\alpha)} - b$$

$$b' = \sqrt{c^2 - b^2}$$

$$c'^2 = a'^2 + b'^2 - 2a'b' \cdot \cos(\gamma')$$

$$\gamma' = 180 - 90 + \alpha$$

In connection with the mobile balancing device according to the invention, it was surprising to find that in the case of this balancing device, which is so configured that it can preferably be worn directly on the body as a belt, particularly in the hip region, and comprises a gyrometer that determines changes in body position three-dimensionally in space as changes in the angular velocity of forward, backward and/or sideward movements of the body, and the signals representing the angular velocity determination is [sic] proportional to the activity of the actuators, and the activation of the actuators is substantially suppressed when the values of the angular velocity are within limits assigned to said angular velocity values on the basis of the movement sequence, the use of gyrometers leads to surprising advantages.

Further advantageous embodiments of the invention will become apparent from the dependent claims.

Preferred variants of the device could take the form, for example, of manual operation of the program selection switch or program selection by voice command; another possibility is for programs to be selected based on analysis of the activity of the musculature or the nervous system.

In another preferred variant of the invention, program implementation is carried out by a set of electrical resistors connected to the program selection switch and to the stimulators.

In another preferred variant, program implementation is provided by means of software that stores a set of attenuations in a microprocessor.

It may also be advantageous if the stimulations are delivered by means of vibrational stimulators.

It may also be preferred for the stimulation to be realized via electrical stimulation applied to the surface of the body or electrical stimulation of motor nerves or the musculature.

It may further be preferred if the stimulation is effected by stimulating sensory nerves or sense organs or portions of the latter.

The device can preferably be attached to the patient's head, torso, thigh, calf, upper arm, lower arm.

In another preferred variant of the invention, it is provided that said attachment to the body is effected by means of a rubber strap or a rubber-fiber-containing fabric strap. Said attachment to the body can also, of course, be effected by means of a leather harness, a fabric hareness or a synthetic leather harness.

The invention is also directed to a method for mobile balance training, wherein changes in the angular velocity in two spatial planes of forward and/or backward movements of the body and/or changes in the angular velocity of sideward movements of the body are determined by means of a sensor, wherein in particular gyrometers can be used, and wherein the signal generated by the sensors and representing the angular velocity measurement is attenuated.

The invention will now be described in greater detail.

Figure 1:
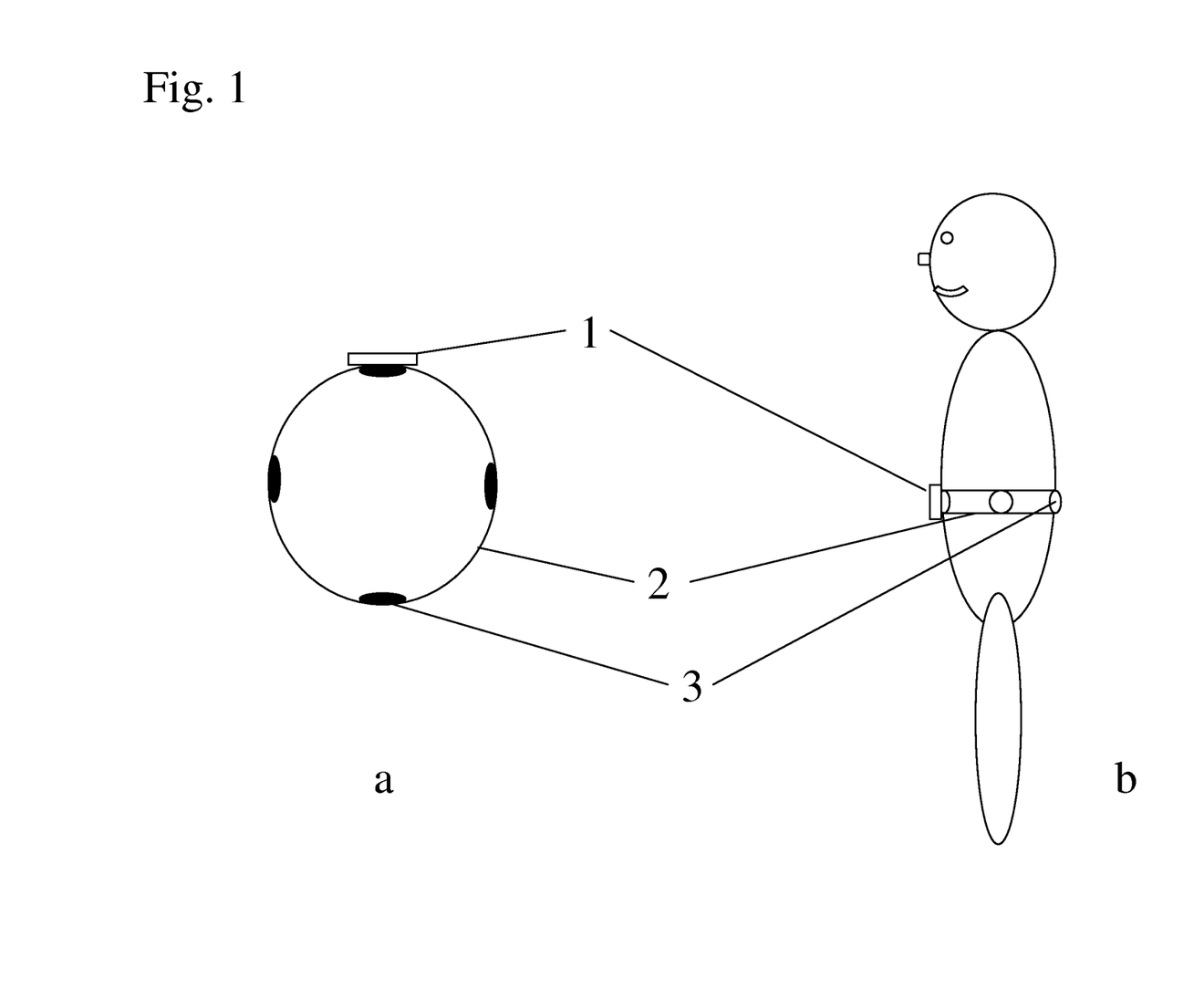
Figure 2:
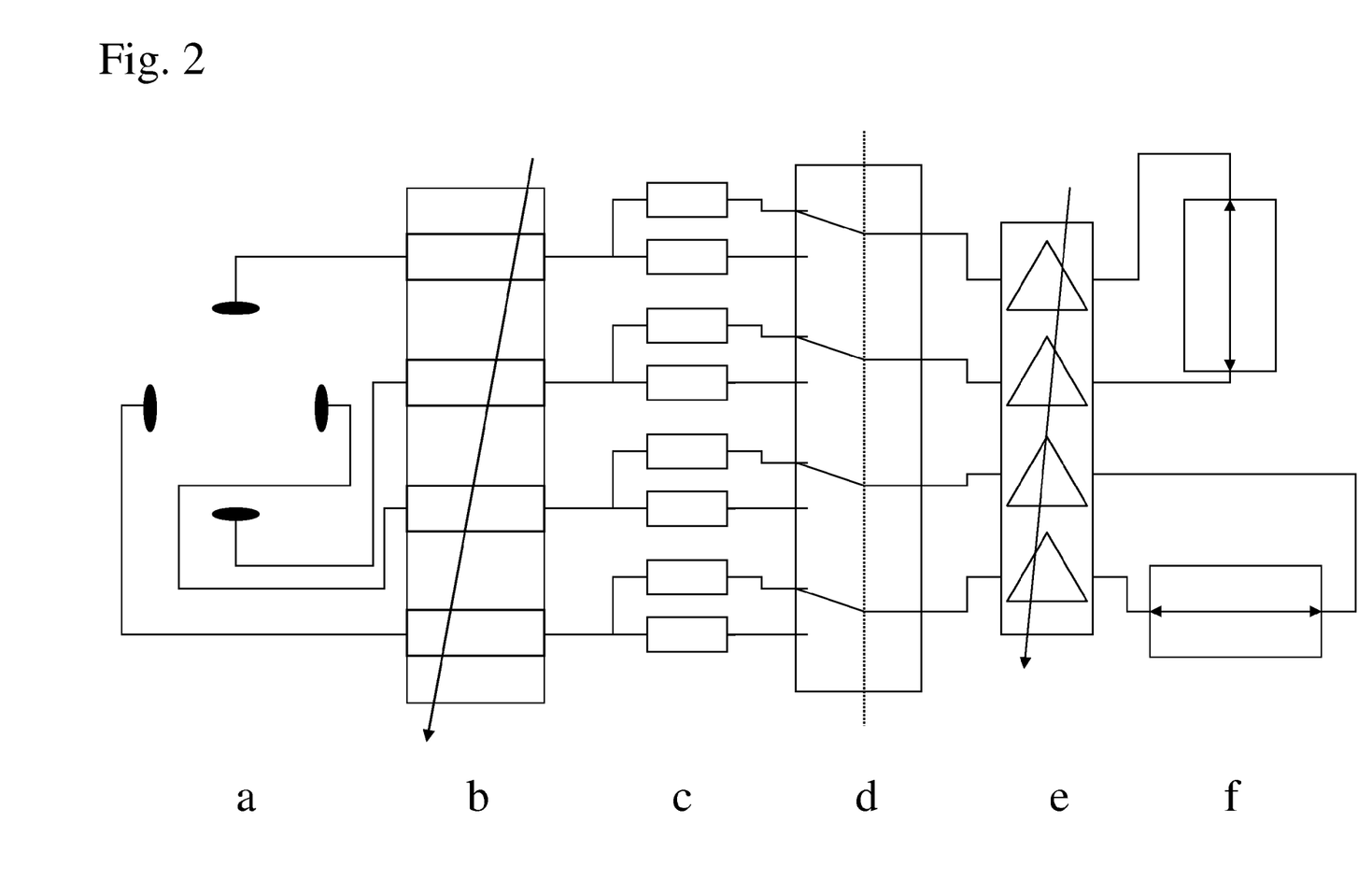

The exemplarily described model of the system depicted in FIG. 1 represents a preferred variant of the invention. In this variant, vibrational stimulators and a measurement and integration unit are worn on a belt around the middle of the body. FIG. 2 exemplarily illustrates the functional wiring diagram of a preferred variant of the invention. The measurement and integration unit contains a sensor for measuring the angular velocity of movements in the forward and backward directions and a sensor for measuring the angular velocity of sideward movements (FIG. 2, Section f). The signal is amplified channel-specifically (channel=direction of movement) (FIG. 2, Section e). The degree of amplification can be adjusted by means of a potentiometer, to adapt the stimulus to the sensitivity of the wearer. The wearer uses a program selection switch (FIG. 2, Section d) to choose the appropriate program for the movement sequence.

In this preferred variant embodiment, the programs contain data regarding the level of the response thresholds of the individual stimulators during specific activities or actions of the wearer. This pattern of stimulator thresholds specific to activities or actions corresponds to the pattern observed in healthy individuals during that particular behavior. A preferred variant in terms of how the pattern of thresholds is implemented in a specific program is a set of electrical resistors that are connected to the program selection switch and to the stimulators (FIG. 2, Section c).

In the preferred variant, adaptation to the wearer's ability to maintain balance in a specific situation is additionally achieved by means of a subtractor—as modulator or adjusting knob—either simultaneously and uniformly or separately for the thresholds of all the stimulators. One option for implementing this adaptation is a stimulator-specific potentiometer (FIG. 2, Section b). Naturally this does not take place, in the preferred variant of the example, in such a way that the actuation of a gyrometer leads automatically (in a linearly proportional manner) to a corresponding linearly proportional actuation of the vibrators or actuators. Since the system of the mobile balancing device can also be used outside the field of medical rehabilitation, in the described preferred variant the actuator motor must be brought to the nominal rotation speed for a period of about 1 second. The frequency (f) preferably should not exceed 35 kHz. Applications of the inventive device outside the medical rehabilitation field are, for example, its use by gymnasts and high divers, who can employ it as a training device. A further application derives from the field of military technology, for example for paratroopers or special forces personnel, who are basically intrinsically healthy in terms of their equilibrium, but have high demands placed on their ability to keep their balance.

According to the functional sequence of the example illustrated in FIG. 2, the intensity of the vibration is proportional to the change in angular velocity, and [the vibration] takes place at the stimulators corresponding to the direction of the threshold-exceeding movement. The following statements are not limited to the examples of FIGS. 1 and 2, but relate to preferred variants of the teaching according to the invention.

Figure 3:
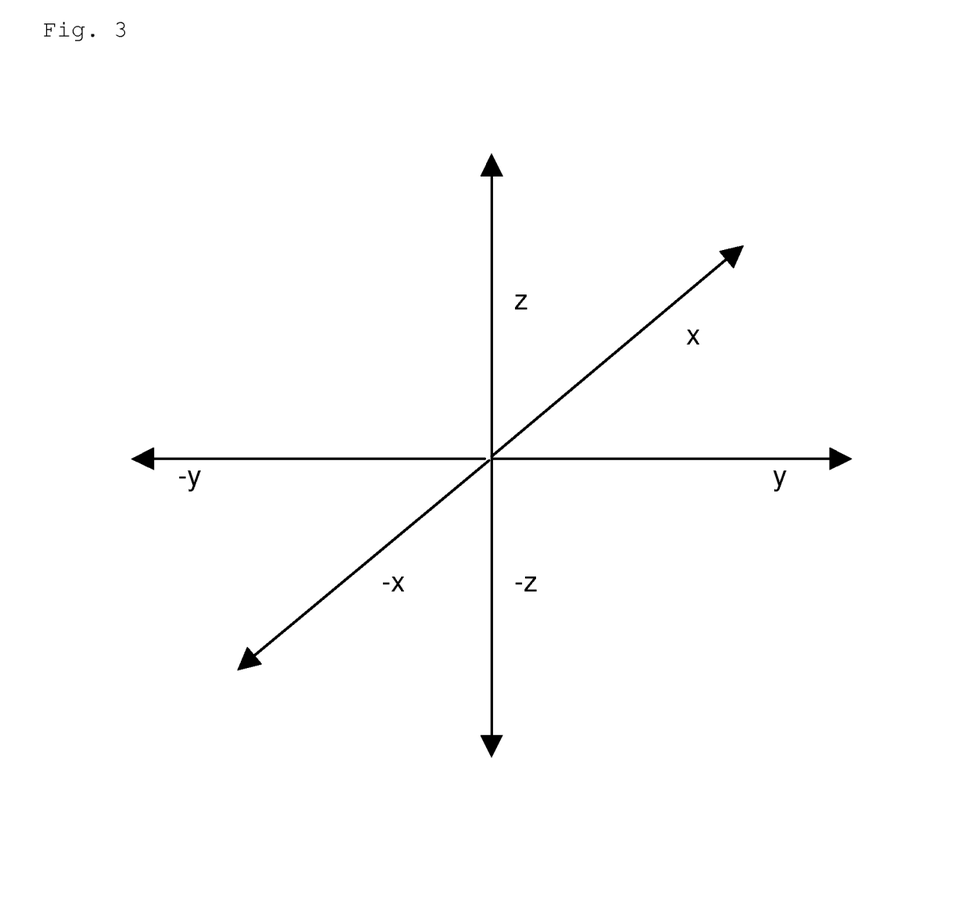
FIG. 3: Spatial reference axes for measurement of three-dimensional movement.
Figure 4:
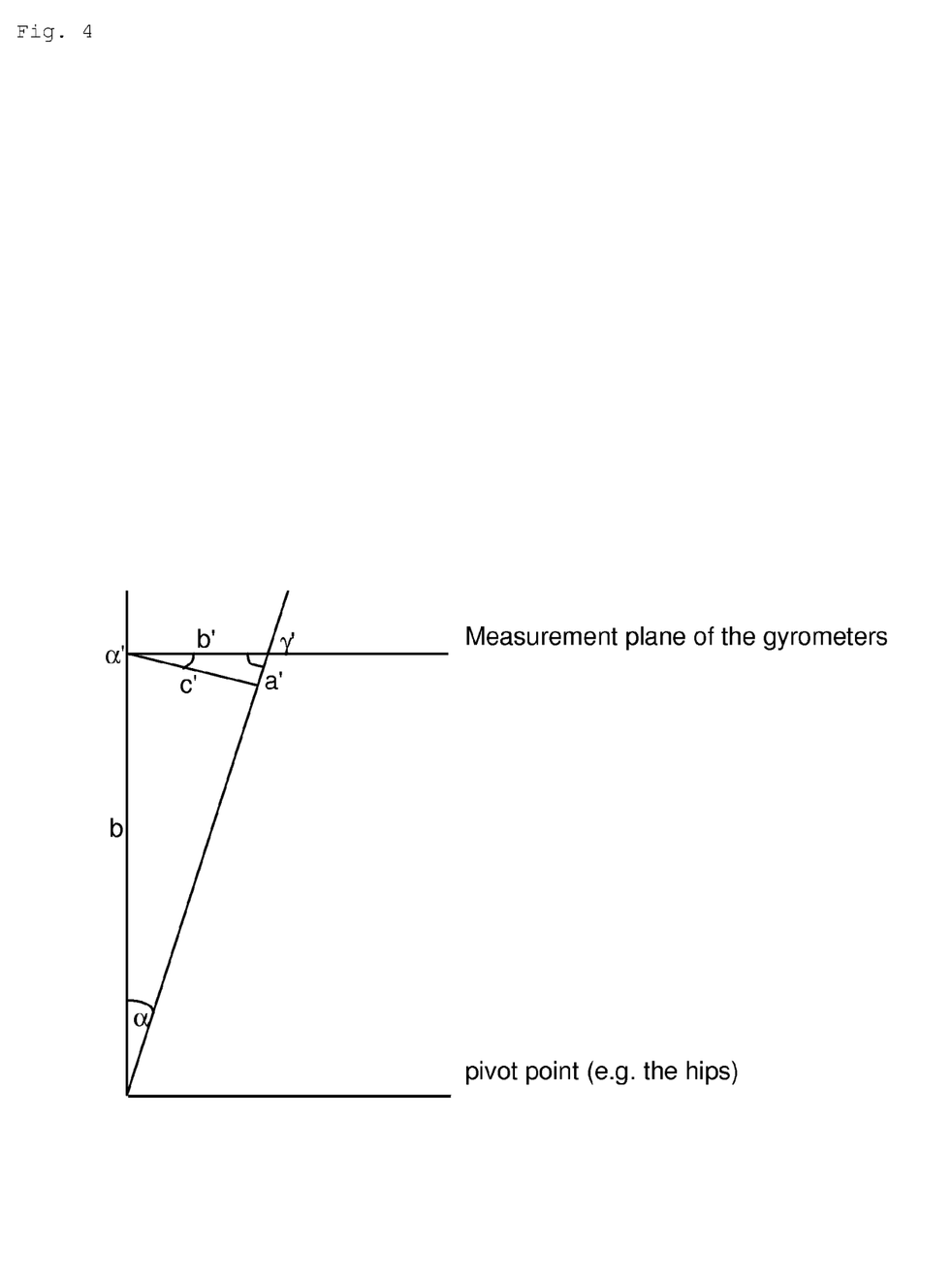
FIG. 4: Diagram and basis of calculation of the values of the third spatial reference axis ($z=\alpha'$) from the data of the other reference axes (x or $y=\alpha$).

In all variant embodiments of the invention, the device can preferably be so configured that two gyrometers whose reference axes (x, y) are perpendicular to each other (FIG. 3) are used. The values for a third reference axis in three-dimensional space (z) (FIG. 3) are calculated in the microprocessor that is present in the device, from data obtained from the other gyrometers, according to the formula given below. The preferred omission of a gyrometer for the z-axis makes it possible to give the device a particularly flat and light construction by virtue of its lower space and power consumption, which is a considerable advantage for use as a mobile, body-part-associated device.

$$\alpha' = \arccos \frac{(b'^2 + c'^2 - a'^2)}{2b'c'}$$

where:

$$a' = \frac{b}{\cos(\alpha)} - b$$

$$b' = \sqrt{c^2 - b^2}$$

$$c'^2 = a'^2 + b'^2 - 2a'b' \cdot \cos(\gamma')$$

$$\gamma' = 180 - 90 + \alpha$$

the foregoing formula being in reference to FIG. 4.

Figure 5:
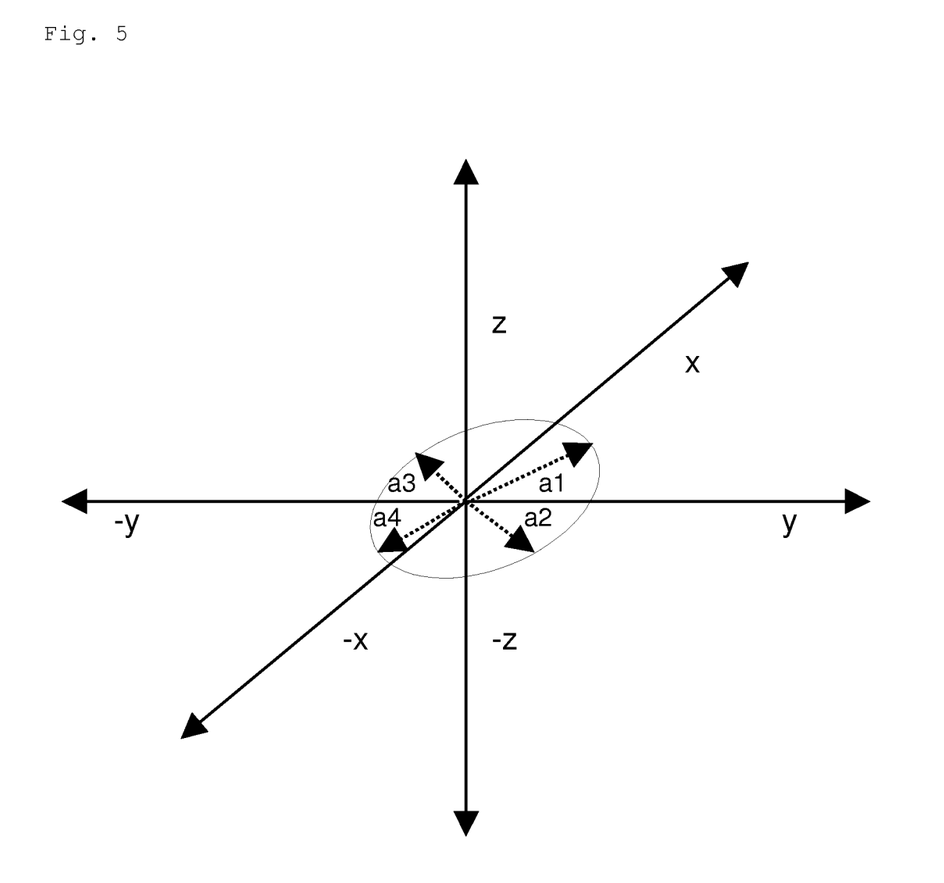
FIG. 5: Representation of the maximum spatial displacement vectors (dashed arrows a1-a4) in each spatial quadrant of an exemplary movement sequence in which the shortest connection between all the spatial displacement vectors forms an ellipse.

The maximum spatial displacement vectors that occur during a specific movement sequence are described in the device by means of the four maximum spatial displacement vectors in each spatial quadrant of a movement sequence. The procedure is illustrated in FIG. 5. The shortest connection between all the spatial displacement vectors in the movement sequence given as an example forms an ellipse that is illustrated in FIG. 5. The dashed arrows (a1-a4) inside the ellipse symbolize the maximum spatial displacement vectors in each quadrant.

The device was used in 100 healthy individuals (48 women, 52 men) to compile age-specific normal values for the maximum displacement vectors in specific movement sequences for each spatial quadrant (a1-a4, see FIG. 5), in the form a=(x, y, z) (Table 1).

TABLE 1

Normal values in °/s for four maximum spatial displacement vectors a1-a4 in the form a = (x, y, z) during specific movement sequences.

Task:

Age qroup: 20-30

| | | | | |
|---|---|---|---|---|
| Standing | a1 = (0.69, 1.36, −0.68) | a2 = (−1.73, 1.36, −0.86) | a3 = (0.69, −1.85, −0.93) | a4 = (−1.73, −1.85, −0.93) |
| Standing in darkness | a1 = (0.81, 1.38, −0.69) | a2 = (−1.90, 1.38, −0.95) | a3 = (0.81, −2.29, −1.14) | a4 = (−1.90, −2.29, −1.14) |

TABLE 1-continued

Normal values in °/s for four maximum spatial displacement vectors a1-a4 in the form a = (x, y, z) during specific movement sequences.

| Task: | | | | |
|---|---|---|---|---|
| Standing on one leg | a1 = (3.35, 3.82, −1.91) | a2 = (−4.36, 3.82, −2.18) | a3 = (3.35, −4.92, −2.46) | a4 = (−4.36, −4.92, −2.46) |
| Standing on one leg in darkness | a1 = (15.98, 22.54, −11.27) | a2 = (−16.16, 22.54, −11.27) | a3 = (15.98, −20.51, −10.26) | a4 = (−16.16, −20.51, −10.26) |
| Balancing | a1 = (13.46, 16.68, −8.34) | a2 = (−20.01, 16.68, −10.01) | a3 = (13.46, −25.55, −12.77) | a4 = (−20.01, −25.55, −12.77) |
| Standing on a soft surface | a1 = (0.71, 1.83, −0.92) | a2 = (−2.46, 1.83, −1.23) | a3 = (0.71, −3.07, −1.53) | a4 = (−2.46, −3.07, −1.53) |
| Standing on a soft surface in darkness | a1 = (0.94, 1.83, −0.91) | a2 = (−2.39, 1.83, −1.20) | a3 = (0.94, −2.69, −1.35) | a4 = (−2.39, −2.69, −1.35) |
| Standing on one leg (soft surface) | a1 = (4.83, 5.95, −2.97) | a2 = (−5.94, 5.95, −2.97) | a3 = (4.83, −6.75, −3.38) | a4 = (−5.94, −6.75, −3.38) |
| Balancing on a soft surface | a1 = (17.19, 24.20, −12.10) | a2 = (−25.17, 24.20, −12.59) | a3 = (17.19, −34.65, −17.32) | a4 = (−25.17, −34.65, −17.32) |
| Walking with lateral head movement | a1 = (20.69, 27.20, −13.60) | a2 = (−25.04, 27.20, −13.60) | a3 = (20.69, −27.43, −13.71) | a4 = (−25.04, −27.43, −13.71) |
| Walking with vertical head movement | a1 = (21.41, 27.13, −13.56) | a2 = (−26.20, 27.13, −13.56) | a3 = (21.41, −32.91, −16.45) | a4 = (−26.20, −32.91, −16.45) |
| Walking in darkness | a1 = (18.19, 25.36, −12.68) | a2 = (−26.82, 25.36, −13.41) | a3 = (18.19, −33.33, −16.66) | a4 = (−26.82, −33.33, −16.66) |
| Climbing stairs | a1 = (29.06, 33.86, −16.93) | a2 = (−32.96, 33.86, −16.93) | a3 = (29.06, −43.91, −21.95) | a4 = (−32.96, −43.91, −21.95) |
| Walking over obstacles | a1 = (37.81, 49.18, 24.59) | a2 = (−36.01, 49.18, 24.59) | a3 = (37.81, −49.13, −24.57) | a4 = (−36.01, −49.13, −24.57) |
| Walking | a1 = (21.23, 27.77, −13.88) | a2 = (−30.11, 27.77, −15.06) | a3 = (21.23, −33.94, −16.97) | a4 = (−30.11, −33.94, −16.97) |
| Sitting down | a1 = (30.77, 26.80, −15.39) | a2 = (−41.64, 26.80, 20.82) | a3 = (30.77, −41.85, −20.93) | a4 = (−41.64, −41.85, −20.93) |
| Standing up | a1 = (53.49, 48.60, 26.75) | a2 = (−29.55, 48.60, 24.30) | a3 = (53.49, −24.24, −26.75) | a4 = (−29.55, −24.24, −14.78) |
| Age qroup: 31-40 | | | | |
| Standing | a1 = (0.92, 1.28, −0.64) | a2 = (−1.75, 1.28, −0.88) | a3 = (0.92, −2.35, −1.17) | a4 = (−1.75, −2.35, −1.17) |
| Standing in darkness | a1 = (0.75, 1.14, −0.57) | a2 = (−1.54, 1.14, −0.77) | a3 = (0.75, −2.00, −1.00) | a4 = (−1.54, −2.00, −1.00) |
| Standing on one leg | a1 = (2.77, 2.95, −1.47) | a2 = (−4.16, 2.95, −2.08) | a3 = (2.77, −3.71, −1.86) | a4 = (−4.16, −3.71, −2.08) |
| Standing on one leg in darkness | a1 = (18.34, 20.18, −10.09) | a2 = (−17.27, 20.18, −10.09) | a3 = (18.34, −19.46, −9.73) | a4 = (−17.27, −19.46, −9.73) |
| Balancing | a1 = (15.30, 16.63, −8.31) | a2 = (−21.55, 16.63, −10.77) | a3 = (15.30, −25.66, −12.83) | a4 = (−21.55, −25.66, −12.83) |
| Standing on a soft surface | a1 = (2.57, 3.15, −1.58) | a2 = (−3.62, 3.15, −1.81) | a3 = (2.57, −3.46, −1.73) | a4 = (−3.62, −3.46, −1.81) |
| Standing on a soft surface in darkness | a1 = (0.94, 1.49, −0.75) | a2 = (−2.24, 1.49, −1.12) | a3 = (0.94, −3.25, −1.62) | a4 = (−2.24, −3.25, −1.62) |
| Standing on one leg (soft surface) | a1 = (8.86, 7.98, −4.43) | a2 = (−10.28, 7.98, −5.14) | a3 = (8.86, −8.01, −4.43) | a4 = (−10.28, −8.01, −5.14) |
| Balancing on a soft surface | a1 = (18.30, 23.97, −11.99) | a2 = (−25.94, 23.97, −12.97) | a3 = (18.30, −32.33, −16.16) | a4 = (−25.94, −32.33, −16.16) |
| Walking with lateral head movement | a1 = (21.60, 26.38, −13.19) | a2 = (−25.29, 26.38, −13.19) | a3 = (21.60, −32.72, −16.36) | a4 = (−25.29, −32.72, −16.36) |
| Walking with vertical head movement | a1 = (21.88, 23.20, −11.60) | a2 = (−21.79, 23.20, −11.60) | a3 = (21.88, −28.50, −14.25) | a4 = (−21.79, −28.50, −14.25) |
| Walking in darkness | a1 = (16.03, 21.38, −10.69) | a2 = (−23.40, 21.38, −11.70) | a3 = (16.03, −28.18, −14.09) | a4 = (−23.40, −28.18, −14.09) |
| Climbing stairs | a1 = (24.62, 39.98, −19.99) | a2 = (−30.64, 39.98, −19.99) | a3 = (24.62, −41.38, −20.69) | a4 = (−30.64, −41.38, −20.69) |
| Walking over obstacles | a1 = (33.25, 55.01, −27.50) | a2 = (−32.23, 55.01, −27.50) | a3 = (33.25, −55.35, −27.67) | a4 = (−32.23, −55.35, −27.67) |
| Walking | a1 = (19.95, 25.43, −12.72) | a2 = (−27.39, 25.43, −13.70) | a3 = (19.95, −31.01, −15.51) | a4 = (−27.39, −31.01, −15.51) |
| Sitting down | a1 = (37.80, 35.72, −18.90) | a2 = (−40.22, 35.72, −20.11) | a3 = (37.80, −43.72, −21.86) | a4 = (−40.22, −43.72, −21.86) |
| Standing up | a1 = (50.08, 49.36, −25.04) | a2 = (−29.87, 49.36, −24.68) | a3 = (50.08, −31.24, −25.04) | a4 = (−29.87, −31.24, −15.62) |
| Age qroup: 41-50 | | | | |
| Standing | a1 = (0.69, 1.08, −0.54) | a2 = (−1.78, 1.08, −0.89) | a3 = (0.69, −2.26, −1.13) | a4 = (−1.78, −2.26, −1.13) |
| Standing in darkness | a1 = (0.65, 1.02, −0.51) | a2 = (−1.88, 1.02, −0.94) | a3 = (0.65, −2.43, −1.22) | a4 = (−1.88, −2.43, −1.22) |
| Standing on one leg | a1 = (6.67, 7.64, −3.82) | a2 = (−7.12, 7.64, −3.82) | a3 = (6.67, −6.76, −3.38) | a4 = (−7.12, −6.76, −3.56) |
| Standing on one leg in darkness | a1 = (26.21, 31.79, −15.90) | a2 = (−25.62, 31.79, −15.90) | a3 = (26.21, −33.98, −16.99) | a4 = (−25.62, −33.98, −16.99) |
| Balancing | a1 = (14.75, 19.55, −9.77) | a2 = (−20.77, 19.55, −10.38) | a3 = (14.75, −32.58, −16.29) | a4 = (−20.77, −32.58, −16.29) |
| Standing on a soft surface | a1 = (1.53, 2.09, −1.05) | a2 = (−2.94, 2.09, −1.47) | a3 = (1.53, −3.53, −1.77) | a4 = (−2.94, −3.53, −1.77) |
| Standing on a soft surface in darkness | a1 = (1.24, 1.46, −0.73) | a2 = (−3.01, 1.46, −1.50) | a3 = (1.24, −3.65, −1.82) | a4 = (−3.01, −3.65, −1.82) |
| Standing on one leg (soft surface) | a1 = (11.88, 13.09, −6.55) | a2 = (−11.16, 13.09, −6.55) | a3 = (11.88, −13.13, −6.57) | a4 = (−11.16, −13.13, −6.57) |
| Balancing on a soft surface | a1 = (20.97, 24.87, −12.43) | a2 = (−26.00, 24.87, −13.00) | a3 = (20.97, −36.75, −18.37) | a4 = (−26.00, −36.75, −18.37) |
| Walking with lateral head movement | a1 = (18.87, 29.07, −14.53) | a2 = (−26.50, 29.07, −14.53) | a3 = (18.87, −30.44, −15.22) | a4 = (−26.50, −30.44, −15.22) |
| Walking with vertical head movement | a1 = (17.83, 22.81, −11.41) | a2 = (−24.71, 22.81, −12.35) | a3 = (17.83, −29.32, −14.66) | a4 = (−24.71, −29.32, −14.66) |
| Walking in darkness | a1 = (16.21, 21.97, −10.98) | a2 = (−23.39, 21.97, −11.69) | a3 = (16.21, −29.72, −14.86) | a4 = (−23.39, −29.72, −14.86) |
| Climbing stairs | a1 = (23.21, 40.15, −20.07) | a2 = (−30.01, 40.15, −20.07) | a3 = (23.21, −46.22, −23.11) | a4 = (−30.01, −46.22, −23.11) |
| Walking over obstacles | a1 = (41.71, 52.30, −26.15) | a2 = (−35.03, 52.30, −26.15) | a3 = (41.71, −53.46, −26.73) | a4 = (−35.03, −53.46, −26.73) |
| Walking | a1 = (17.78, 26.08, −13.04) | a2 = (−27.76, 26.08, −13.88) | a3 = (17.78, −32.92, −16.46) | a4 = (−27.76, −32.92, −16.46) |
| Sitting down | a1 = (38.42, 31.36, −19.21) | a2 = (−46.14, 31.36, −23.07) | a3 = (38.42, −45.03, −22.51) | a4 = (−46.14, −45.03, −23.07) |

TABLE 1-continued

Normal values in °/s for four maximum spatial displacement vectors a1-a4 in the form a = (x, y, z) during specific movement sequences.

| Task: | | | | |
|---|---|---|---|---|
| Standing up Age group: 51-60 | a1 = (54.58, 46.19, −27.29) | a2 = (−33.15, 46.19, −23.09) | a3 = (54.58, −28.31, −27.29) | a4 = (−33.15, −28.31, −16.58) |
| Standing | a1 = (1.31, 1.18, −0.66) | a2 = (−1.82, 1.18, −0.91) | a3 = (1.31, −2.83, −1.42) | a4 = (−1.82, −2.83, −1.42) |
| Standing in darkness | a1 = (0.90, 1.10, −0.55) | a2 = (−1.83, 1.10, −0.92) | a3 = (0.90, −2.53, −1.26) | a4 = (−1.83, −2.53, −1.26) |
| Standing on one leg | a1 = (3.83, 5.00, −2.50) | a2 = (−4.28, 5.00, −2.50) | a3 = (3.83, −5.76, −2.88) | a4 = (−4.28, −5.76, −2.88) |
| Standing on one leg in darkness | a1 = (23.80, 35.06, −17.53) | a2 = (−24.60, 35.06, −17.53) | a3 = (23.80, −30.47, −15.23) | a4 = (−24.60, −30.47, −15.23) |
| Balancing | a1 = (15.06, 18.79, −9.39) | a2 = (−19.62, 18.79, −9.81) | a3 = (15.06, −27.10, −13.55) | a4 = (−19.62, −27.10, −13.55) |
| Standing on a soft surface | a1 = (1.60, 1.58, −0.80) | a2 = (−3.23, 1.58, −1.61) | a3 = (1.60, −3.75, −1.87) | a4 = (−3.23, −3.75, −1.87) |
| Standing on a soft surface in darkness | a1 = (1.56, 1.92, −0.96) | a2 = (−2.76, 1.92, −1.38) | a3 = (1.56, −3.34, −1.67) | a4 = (−2.76, −3.34, −1.67) |
| Standing on one leg (soft surface) | a1 = (15.44, 17.67, −8.83) | a2 = (−16.37, 17.67, −8.83) | a3 = (15.44, −16.27, −8.13) | a4 = (−16.37, −16.27, −8.18) |
| Balancing on a soft surface | a1 = (24.61, 26.51, −13.25) | a2 = (−22.83, 26.51, −13.25) | a3 = (24.61, −29.69, −14.84) | a4 = (−22.83, −29.69, −14.84) |
| Walking with lateral head movement | a1 = (22.53, 31.92, −15.96) | a2 = (−24.79, 31.92, −15.96) | a3 = (22.53, −31.95, −15.97) | a4 = (−24.79, −31.95, −15.97) |
| Walking with vertical head movement | a1 = (16.52, 22.94, −11.47) | a2 = (−21.48, 22.94, −11.47) | a3 = (16.52, −24.11, −12.06) | a4 = (−21.48, −24.11, −12.06) |
| Walking in darkness | a1 = (16.14, 20.72, −10.36) | a2 = (−20.44, 20.72, −10.36) | a3 = (16.14, −23.97, −11.98) | a4 = (−20.44, −23.97, −11.98) |
| Climbing stairs | a1 = (26.53, 44.67, −22.34) | a2 = (−27.79, 44.67, −22.34) | a3 = (26.53, −39.80, −19.90) | a4 = (−27.79, −39.80, −19.90) |
| Walking over obstacles | a1 = (43.24, 71.09, −35.55) | a2 = (−34.88, 71.09, −35.55) | a3 = (43.24, −61.64, −30.82) | a4 = (−34.88, −61.64, −30.82) |
| Walking | a1 = (19.36, 28.46, −14.23) | a2 = (−25.80, 28.46, −14.23) | a3 = (19.36, −29.91, −14.95) | a4 = (−25.80, −29.91, −14.95) |
| Sitting down | a1 = (44.06, 42.20, −22.03) | a2 = (−40.96, 42.20, −21.10) | a3 = (44.06, −46.81, −23.41) | a4 = (−40.96, −46.81, −23.41) |
| Standing up | a1 = (51.90, 55.69, −27.84) | a2 = (−35.93, 55.69, −27.84) | a3 = (51.90, −38.22, −25.95) | a4 = (−35.93, −38.22, −19.11) |

In contrast to other measurement systems for determining body movements, the device according to the invention takes account of the fact that the displacement of the body's center of gravity depends on the magnitude of the particular displacement vectors, in the form $f(x)=ax^2$. Previous systems erroneously posited a linear relationship. The likelihood of no longer being able to control the body's center of gravity was grossly underestimated as a result. The nonlinear (power function) displacement of the body's center of gravity in each spatial quadrant can easily be calculated by means of the spatial displacement vectors. Using the compiled normal values (Table 1), a formula for this was established on the basis of sin $\alpha'/c'$ (see FIG. 4), in the form $f(x)=0.0017x^{1.9462}$. A further advantage of the device is that this relationship is not taken into account globally when activating the stimulators, but is considered as a function of the age- and task-specific normal values, particularly those of the z-axis. In this operation, the factor representing the relationship between the displacement of the body's center of gravity and the particular displacement vectors is multiplied by the quotient of the age- and task-specific normal value of the displacement vector of the z-axis and the measured value of the displacement vector of the z-axis. The calculation is as follows:

$$f = \frac{z}{z_{normal\ value}} * 0.0017x^{1.9462}$$

where x is the values of the particular displacement vector of the form
a=(x, y, z) when x>y. If y>x, then the value of y is used in the calculation.

The result (f) is added to the value x (if x>y) or y (if y>x) of the corresponding displacement vector of a spatial quadrant. Thus, the nonlinear increase in the displacement of the body's center of gravity as the body leans is estimated precisely and is taken into account with regard to the stimulation. The advantages of the exemplarily described system apply to all of the technical teaching of the invention. The term "device" means any preferred device of the invention, and is not limited to the devices cited by way of example.

FIGS. 1 to 5 show the following:

FIG. 1a-b: Vibrational stimulators and a measurement and integration unit worn on a belt around the middle of the body.

FIG. 2 a-f: Functional wiring diagram of a preferred variant of the invention.

The invention claimed is:

1. A mobile balancing device comprising:
actuators configured to be placed on a body, and
at least one measurement and integration unit comprising
two gyrometers that are configured to determine changes in body position three-dimensionally in space as changes in angular velocity of forward, backward and/or sideward movements of the body and wherein two of said two gyrometers provide signals representing an angular velocity determination, wherein said signals are proportional to an activity of said actuators and wherein activation of said actuators is suppressed when the values of the angular velocity are within limits that are based on a movement sequence, wherein said two gyrometers are disposed orthogonally to each other and are configured to acquire measurement data two-dimensionally and the mobile balancing device is configured so that the data of only two of said gyrometers that are disposed orthogonally is then converted to a three-dimensional spatial presentation.

2. The balancing device of claim 1, wherein
one or both of said gyrometers are selected from a group comprising AD×RS 150EB.

3. The balancing device of claim 1, wherein
said actuators are balance-wheel motors.

4. The balancing device of claim 3, wherein
a rotation speed of a said balance-wheel motor depends on a frequency of an outgoing pulse, said frequency of said pulse being given by $$f[1/S] = \frac{X[°/s]}{1.8°} \times 64,$$

wherein X [°/s]=desired angular velocity;
1.8°=basic resolution of step width of said motor; and
64=fine resolution of said basic resolution of said step width of said motor.

5. The balancing device of claim 1, wherein
movements of the body are determined as displacement vectors by said gyrometers that are disposed orthogonally to each other.

6. The balancing device of claim 1,
further comprising a rubber strap, a rubber-fiber-containing fabric strap, a leather harness, a fabric harness or a synthetic leather harness to position it on and/or to attach it to the body.

7. The balancing device of claim 1 further comprising
a manually operable program switch for selecting a program.

8. The balancing device of claim 1, wherein
said balancing device comprises different programs, and wherein
a selection between said programs is effected by voice command and/or by analyzing an activity of the body's musculature or of the body's nervous system.

9. The balancing device of claim 7, wherein
an implementation of a program is effected by a set of electrical resistors that are connected to said program switch and said actuators.

10. The balancing device of claim 1, wherein
implementation of a program is effected via software that stores a set of attenuations of said signals in a microprocessor.

11. The balancing device of claim 1, wherein
said actuators are vibrational actuators, and said actuators are being actuated by electrical stimulation applied to a surface of the body, by electrical stimulation of motor nerves or of the body's musculature and/or by electrical stimulation of sensory nerves or sense organs or portions of the latter.

12. The balancing device of claim 1, wherein
said changes in body position are calculated as follows for a third reference axis:

$$\alpha' = \arccos\frac{(b'^2 + c'^2 - a'^2)}{2b'c'}$$

wherein:
α' is the change of body position for a third reference axis, $$a' = \frac{b}{\cos(\alpha)} - b$$
$$b' = \sqrt{c^2 - b^2}$$
$$c'^2 = a'^2 + b'^2 - 2a'b' \cdot \cos(\gamma')$$
$$\gamma' = 180 - 90 + \alpha,$$

wherein α is the change of body position for a first reference axis relative to a second reference axis,
wherein b and c define α and b' and c' define α', wherein α is measured at a pivot point of the body and wherein b' defines a measurement plane of the gyrometer and wherein b is represented by a line that extends perpendicular from b' and ends in said pivot point and wherein c is represented by a line that extends from the pivot point at an angle α in plane with b to intersect with b' at an angle γ'.

13. Method for balance training of a body comprising placing the balancing device of claim 1 on the body and balance training the body.

14. A method for the mobile balance training of a body, comprising
providing the mobile balancing device of claim 1
wherein the changes in angular velocity are determined via sensor(s), and wherein the signal generated by the sensors and representing the angular velocity measurements is attenuated.

15. The balancing device of claim 1,
wherein said balancing device is so configured that it can be worn directly on the body as a belt.

16. The balancing device of claim 15, wherein said belt is to be worn in the body's hip region.

17. The balancing device of claim 1, wherein the limits that are based on a movement sequence are normal values of a spatial displacement vector for a specific movement sequence.

18. A mobile balancing device comprising
actuators configured to be placed on a body,
gyrometers configured to determine changes in a position of the body three dimensionally in space as change in angular velocity of forward, backward and/or sideward movements of the body to provide signals representing an angular velocity determination wherein said signals are proportional to an activity of said actuators and wherein the mobile balancing device is configured to (i) suppress activation of said actuators when the values of the angular velocity are within limits that are based on a movement sequence, (ii) detect movements of the body as changes in angular velocity, (iii) represent the movements as displacement vectors and (iv) determine displacement of the body's center of gravity by a non-linear function from said displacement vectors, wherein the non-linear function is f(x)=ax², wherein x is the value of the displacement vector, in form of a=(x,y,z) when x>y, when y>x, the value of y is used in place of x, with x being the first, y the second and z the third spatial reference axis.

19. A mobile balancing device comprising
actuators configured to be placed on a body,
gyrometers configured to determine changes in a position of the body three dimensionally in space as change in angular velocity of forward, backward and/or sideward movements of the body to provide signals representing an angular velocity determination wherein said signals are proportional to an activity of said actuators and wherein the mobile balancing device is configured to (i) suppress activation of said actuators when the values of the angular velocity are within limits that are based on a movement sequence, (ii) detect movements of the body as changes in angular velocity, (iii) represent the movements as displacement vectors and (iv) determine displacement of the body's center of gravity by a non-linear function from said displacement vectors wherein the non-linear function is:

$$f = \frac{z}{z_{normal\ value}} * 0.0017 x^{1.9462},$$

wherein, with z is the third spatial reference axis (z-axis) and $z_{normal}$ value is the age- and task-specific normal value of the z-axis.

\* \* \* \* \*